United States Patent [19]

Erpenbach et al.

[11] Patent Number: 4,629,711

[45] Date of Patent: Dec. 16, 1986

[54] PROCESS FOR PURIFYING AND RECOVERING CONTAMINATED CATALYST SOLUTION OBTAINED IN THE CARBONYLATION OF METHYL ACETATE AND/OR DIMETHYLETHER

[75] Inventors: Heinz Erpenbach, Cologne; Klaus Gehrmann; Winfried Lork, both of Erftstadt; Peter Prinz, Hürth, all of Fed. Rep. of Germany

[73] Assignee: Hoechst Aktiengesellschaft, Fed. Rep. of Germany

[21] Appl. No.: 852,222

[22] Filed: Apr. 15, 1986

[30] Foreign Application Priority Data

Apr. 29, 1985 [DE] Fed. Rep. of Germany ....... 3515396

[51] Int. Cl.$^4$ .................... B01J 31/40; B01J 38/68; C07C 51/56; C01G 55/00
[52] U.S. Cl. ...................... 502/24; 260/546; 260/549; 502/32; 502/33; 560/232; 423/22
[58] Field of Search .............. 502/24, 32, 33; 260/549, 546; 560/232; 423/22

[56] References Cited

U.S. PATENT DOCUMENTS

| | | | |
|---|---|---|---|
| 4,388,217 | 6/1983 | Hembre et al. | 260/549 |
| 4,440,570 | 4/1984 | Erpenbach et al. | 502/24 |
| 4,442,304 | 4/1984 | Erpenbach et al. | 502/24 |
| 4,556,644 | 12/1985 | Erpenbach et al. | 502/33 |
| 4,557,760 | 12/1985 | Erpenbach et al. | 502/24 |

FOREIGN PATENT DOCUMENTS 1173018 8/1984 Canada ................... 502/33

Primary Examiner—P. E. Konopka
Attorney, Agent, or Firm—Connolly and Hutz

[57] ABSTRACT

Catalyst solution contaminated during the carbonylation of methyl acetate and/or dimethylether, containing carbonyl complexes of rhodium, quaternary heterocyclic aromatic nitrogen compounds or quaternary organophosphorus compounds as organic promoters, undistillable organic contaminants, acetic acid, acetic anhydride and ethylidene diacetate, is purified and recovered. To this end the contaminated catalyst solution is extracted with a dialkylether having from 1–4 carbon atoms and thereby freed from its organic contaminants, acetic acid, acetic anhydride and ethylidene diacetate, and the ether phase is separated from a precipitated promoter-containing catalyst complex; the ether phase is treated with iodine and/or methyl iodide, a further portion of precipitated promoter-containing catalyst complex is separated and united with the purified catalyst complex; the ether phase is distillatively separated into its constituents, recovered dialkylether is used for extraction, and fresh catalyst solution is prepared from the recovered mixture of acetic acid, acetic anhydride and ethylidene diacetate and united purified catalyst complex, and the organic contaminants retained in the residue coming from the ether phase distillation are expelled, and the purified catalyst is distillatively freed from residual dialkylether.

6 Claims, No Drawings

PROCESS FOR PURIFYING AND RECOVERING CONTAMINATED CATALYST SOLUTION OBTAINED IN THE CARBONYLATION OF METHYL ACETATE AND/OR DIMETHYLETHER

This invention relates to a process for purifying and recovering a catalyst solution contaminated during the carbonylation of methyl acetate and/or dimethylether, containing carbonyl complexes of rhodium, quaternary heterocyclic aromatic nitrogen compounds or quaternary organophosphorus compounds as organic promoters, and optionally also compounds of non noble metals yielding carbonyl compounds as inorganic promoters, undistillable organic contaminants as well as acetic acid, acetic anhydride and ethylidene diacetate.

Rhodium is a noble metal catalyst widely used in the form of various complex compounds in hydroformylation and carbonylation reactions. As a result of the fact that rhodium is available in limited quantities only, it is a very expensive noble metal for which it is highly desirable to be recovered or for its complex compounds present in a catalyst system contaminated, or still products obtained in the above reactions to be purified; this has repeatedly been described in the literature.

The process disclosed in EP-A-0 073 922 and 0 073 342 evidence the different dissolution behaviour for a complex Rh-catalyst and for tarry matter obtained therein. The two processes disclose purifying and recovering a catalyst solution of a rhodium/phosphonium or rhodium/ammonium-carbonyl complex contaminated during the carbonylation of methyl acetate and/or dimethylether. In the two processes, the contaminated catalyst solution is initially freed from its volatile constituents. In the process disclosed in EP-A-O 073 922, the residue is subsequently freed from organic contaminants by extraction with an aliphatic ether. In the process disclosed in EP-A-0 073 342, the residue remaining behind after separation of the volatile constituents is water-treated and initially separated into water-soluble organic promoter and water-insoluble mixture of rhodium/carbonyl-complex and organic contaminants. Next, the organic contaminants are dissolved out from the water-insoluble residue using an aliphatic ether. In the two cases, the noble metal/carbonyl complex is preserved and used again in the reaction cycle, whilst the residues are isolated from the respective ether phase in yields of more than 90%. The rhodium or noble metal is recoverable in yields of from 98.8 to 99.6%.

EP-A-0 128 439 discloses a process permitting the catalyst complex used in and contaminated during the carbonylation of methyl acetate and/or dimethylether to be worked up so that the noble metal of group VIII becomes precipitated in elementary form and recovered in yields of more than 99.9%, based on the noble metal quantity used, undistillable organic contaminants being extracted using an ethyleneglycoldialkyl ether of the formula $R(OC_2H_4)_n$—OR (n=1-4). Prior to reusing the rhodium in the reaction, it is necessary for the elementary rhodium to be converted to a soluble Rh/carbonyl-complex.

The recent steep increase in price noted for rhodium makes it invariably necessary for a rhodium catalyst used in a commercial process to be recovered substantially without loss of rhodium. This is also true concerning the purification and recovery of a contaminated rhodium catalyst which is definitely required to be recycled quantitatively. It is therefore an imperative requirement for the organic residue formed during the process to be separated from the catalyst solution substantially without loss of Rh, in fairly simple fashion involving no intermediary processing stages, and for the purified catalyst system to be directly reused in the reaction.

These are requirements which are largely but not quantitatively complied with by the processes disclosed in EP-A 0 073 922, 0 073 342 and 0 128 439. In the first two cases, Rh is obtained in a yield of at most 99.8 %, the Rh/carbonyl complex remaining undestroyed; in the third case, the Rh-yield can be increased to even more than 99.9 %, after purification. In this latter case, however, rhodium in metallic form is obtained as already mentioned hereinabove, for which it is necessary to be subjected to an additional processing step for conversion to complex material.

All of the above requirements are met by the process of this invention which unexpectedly permits the catalyst solution contaminated during the carbonylation of methyl acetate and/or dimethylether to be worked up by simple distilling and extracting steps so that it is possible for the undistillable organic contaminants to be separated from the catalyst solution without loss of rhodium and destruction of the Rh/carbonyl complex and promoter. In other words, the Rh/carbonyl-complex and promoter salt can be recycled into the carbonylation stage without being subjected to expensive preparatory treatment. By the circulation of the extractants used for work up, waste materials are additionally prevented from polluting the environment. Only undistillable organic contaminants formed during the process are separated and can be disposed of in accordance with the most recent art in this field.

The process of this invention comprises more particularly: subjecting the contaminated catalyst solution in a first processing stage to extraction with a dialkylether having from 1-4 carbon atoms and thereby freeing it from its organic contaminants, from acetic acid, acetic anhydride and ethylidene diacetate, and separating the ether phase from a precipitated promoter-containing catalyst complex; treating the ether phase in a second processing stage with iodine and/or methyl iodide, separating a further portion of precipitated promoter-containing catalyst complex and uniting it with the purified catalyst complex from the first processing stage; separating the ether phase into its constituents by distilling it, using recovered dialkylether again in the extraction of the first processing stage, preparing fresh catalyst solution from the recovered mixture of acetic acid, acetic anhydride and ethylidene diacetate and united purified catalyst complex, and expelling the organic contaminants retained in the residue of the ether phase distillation and distillatively freeing the purified catalyst solution from residual dialkylether.

Further preferred and optional features of the process of this invention provide:

(a) for the catalyst solution to be extracted with the dialkylether and the ether phase to be treated with iodine and/or methyl iodide at temperatures of 20°–140° C. and under pressures of 1–30 bars;

(b) for 0.5–20 parts by weight dialkylether to be used per part by weight contaminated catalyst solution;

(c) for 0.00005–0.01 part by weight iodine and/or methyl iodide to be used par part by weight dialkylether;

(d) for the first and second processing stages to be combined by treating the contaminated catalyst solution with iodine and/or methyl iodide and dialkylether and the ether phase to be separated from the precipitated promoter-containing catalyst complex;

(e) for 0.0001–0.01 part by weight iodine and/or methyl iodide to be used per part by weight contaminated catalyst solution.

The contaminated catalyst solution is more particularly obtained as follows: the reaction mixture coming from a carbonylation reactor is distillatively separated into the final products targeted, especially acetic anhydride, acetic acid and/or ethylidene diacetate and unreacted cycled feed materials on the one hand, and into cycled catalyst solution which is the still product, on the other. A partial stream of that catalyst solution which may contain up to 50 mass % acetic anhydride, acetic acid and/or ethylidene diacetate, depending on the processing conditions selected, and which becomes contaminated with the passage of time with undistillable organic products is taken from the catalyst cycle and purified. The contaminated catalyst solution contains the noble metal rhodium as a carbonyl complex e.g. $[CH_3P(C_4H_9)_3]Rh(CO)I_4$ or $[CH_3P(C_4H_9)_3]Rh(CO)_2I_2$ The catalyst preferably also contains as an organic promoter one or more of the following heterocyclic armomatic nitrogen compounds or organophosphorus compounds:

1. N-methylpyridinium iodide, N,N-dimethylimidazolium iodide, N-methyl-3-picolinium iodide, N-methyl-2,4-lutidinium iodide, N-methyl-3,4-lutidinium iodide, N-methyl-quinolinium iodide;
2. tri-n-butylmethylphosphonium iodide, trioctylmethylphosphonium iodide, trilaurylmethylphosphonium iodide, triphenylmethylphosphonium iodide.

Finally, the catalyst solution may also contain an inorganic promoter selected from the carbonyl-yielding non noble metals Ce, Ti, Zr, Hf, Ge, Sn, Pb, V, Nb, Ta, As, Sb, Bi, Cr, Mo, W, Mn, Re, Fe, Co, Ni.

The contaminated catalyst solution coming from the reactor is extracted with the dialkylether, preferably at 20°–140° C. (1–30 bars). During that treatment, the undistillable organic contaminants formed during the reaction and the portions of acetic anhydride, acetic acid and/or ethylidene diacetate retained in the catalyst solution are dissolved whilst the Rh-carbonyl complex together with the promoter(s) remains behind as an undissolved catalyst phase. Next, the ether phase is aftertreated with addition of iodine and/or methyl iodide, preferably at 20°–140° C. (1–30 bars) and a precipitate containing rhodium is obtained, which is separated and added to the purified catalyst phase. After separation of the precipitate from the ether phase, the ether is recovered by distillation and recycled to the extraction stage. Next, acetic anhydride, acetic acid and/or ethylidene diacetate are redistilled, the undistillable organic contaminants remaining as residue. The redistilled reaction products are used for dissolving the purified catalyst phase (Rh/carbonyl-complex and promoter salt), freed from adhering ether, if any, and recycled into the carbonylation stage. The undistillable organic contaminants are incinerated, for example.

The process of this invention can be carried out continuously or discontinuously.

EXAMPLE 1

1000 g catalyst solution composed of 6.42 mass % rhodium/carbonyl-complex $[CH_3P(C_4H_9)_3]$ $[Rh(CO)_2I_2]$ (corresponding to 10.5 g = 1.05 mass % Rh), 67.38 mass % methyl-tri-n-butyl-phosphonium iodide, 6.2 mass % organic contaminants, 6.6 mass % acetic acid, 13.3 mass % acetic anhydride and 0.1 mass % ethylidene diacetate was taken from the catalyst cycle of a dimethylether carbonylation stage to be freed from organic contaminants; to this end, the catalyst solution was added dropwise within 30 minutes with agitation to 3000 g diisopropylether (bp = 67.5° C.). Agitation was continued for a further 30 minutes, the ether phase was separated from precipitated catalyst complex containing promoter, admixed with 0.8 g elementary iodine and boiled under reflux for 2 hours at 70° C. A precipitate containing Rh was obtained. It was filtered and added to the catalyst complex. Next, the filtered ether phase was distillatively separated into 2980 g diisopropylether, 65 g acetic acid, 131 g acetic anhydride, 1 g ethylidene diacetate and 55.9 g undistillable organic contaminants as a tarry residue (containing 0.005 mass % Rh). The mixture of acetic acid, ethylidene diacetate and acetic anhydride so recovered was used for dissolving the purified promoter-containing catalyst complex while heating and, if desired, injecting CO. A further 20 g diisopropylether was distilled off whilst 945 g purified catalyst solution containing 10.5 g Rh remained behind; it was added to the catalyst cycle. The two ether distillates were united and used again in the extraction stage. After purification of the contaminated catalyst solution taken from the cycle, 99.97 % rhodium was recycled into the carbonylation stage.

EXAMPLE 2

(COMPARATIVE EXAMPLE)

1000 g contaminated catalyst solution with the composition indicated in Example 1 was taken from the catalyst cycle of the dimethylether carbonylation stage to be freed from its organic contaminants; to this end, it was added dropwise with agitation within 30 minutes to 3000 g diisopropylether. Agitation was continued for a further 30 minutes, and the ether phase was separated from the precipitated catalyst complex containing promoter, by filtration. The filtered ether phase was distillatively separated without being subjected to treatment with iodine, into 2980 g diisopropylether, 197 g acetic acid/acetic anhydride/ethylidene diacetate-mixture and 56.1 g undistillable organic contaminants as residue (containing 0.45 mass % Rh). The purified precipitated catalyst complex was dissolved while heating in the AcOH/Ac2O/EDA-mixture recovered from the ether phase, while a further 20 g diisopropylether was distilled off. 944 g purified catalyst solution containing 10.25 g Rh for reuse was obtained. Only 97.6% rhodium was recycled into the carbonylation stage.

EXAMPLE 3

1000 g catalyst solution composed of 5.6 mass % Rh/carbonyl-complex $C_5H_9N_2$ $[Rh(CO)_2I_2]$ (corresponding to 11.3 g = 1.13 mass % Rh), 70.0 mass % N,N-dimethylimidazolium iodide ($C_5H_9N_2I$), 8.1 mass % organic contaminants, 16.3 mass % acetic acid, acetic anhydride and ethylidene diacetate was taken from the catalyst cycle of a methyl acetate carbonylation stage and metered with agitation within 15 minutes into 4000 g diethylether (bp=34.6° C.). Agitation was continued for a further 30 minutes and the ether phase was removed from the precipitated catalyst complex containing promoter, admixed with 4 g methyl iodide and boiled under reflux for 2 hours at 36° C. A precipitate containing Rh was obtained; it was separated and added to the catalyst complex. Next, the ether phase freed from the Rh-containing precipitate was separated into 3930 g diethylether, 160 g acetic acid/acetic anhydride/EDA-mixture and 75.1 g organic contaminants (containing 0.007 mass % Rh) which were removed. The organic contaminants were incinerated whilst the acetic acid/acetic anhydride/EDA-mixture obtained was used as a solvent for the united purified catalyst complex. The catalyst complex containing promoter was dissolved, 70 g diethylether was distilled off and 929 g purified catalyst solution containing 11.3 g Rh was recycled into the carbonylation stage. 99.95 % Rh was recycled. The two ether distillates were united and used again in the extraction stage.

EXAMPLE 4

1000 g catalyst solution composed of 6.0 mass % Rh/carbonyl-complex [CH$_3$P(C$_4$H$_9$)$_3$] [Rh(CO)$_2$I$_2$] (corresponding to 9.8 g=0.98 mass % Rh), 62.1 mass % methyl-tri-n-butylphosphonium iodide, 7.3 mass % organic contaminants, 24.6 mass % acetic acid and acetic anhydride was taken from the catalyst cycle of the methyl acetate carbonylation stage to be freed from its organic contaminants; to this end, it was admixed with 6 g elementary iodine, heated while stirring for 0.5 h to 110° C. and then added while stirring to 3500 g di-n-propylether (bp=91° C.). Stirring was continued for a further 30 minutes at 90° C. and the precipitated catalyst complex containing promoter was separated from the ether phase. 3450 g di-n-propylether, 242 g acetic acid and acetic anhydride, and 67.2 g undistillable organic contaminants (containing 0.007 mass % Rh) were recovered from the ether phase. The organic contaminants were discarded whereas the acetic acid/acetic anhydride-mixture recovered from the ether extract was used for dissolving the purified catalyst complex containing promoter. A further 50 g residual di-n-propylether was distilled off and 939 g purified catalyst solution containing 9.8 g Rh was recycled into the carbonylation stage; the rhodium was recycled at a rate of 99.95 %. The united ether distillates were recycled into the extraction stage.

EXAMPLE 5

1000 g catalyst solution composed of 8.08 mass % Rh/carbonyl complexes [CH$_3$P(C$_4$H$_9$)$_3$] [Rh(CO)$_2$I$_2$] and [CH$_3$P(C$_4$H$_9$)$_3$] [RhCOI$_4$] in the ratio of 1:1 (corresponding to 11.2 g=1.12 mass % Rh), 49.22 mass % methyl-tri-n-butylphosphonium iodide, 5.9 % organic contaminants, 36.8 mass % acetic acid, acetic anhydride and ethylidene diacetate was taken from the catalyst cycle of the dimethylether carbonylation stage to be freed from its organic contaminants; to this end, it was metered while stirring within 30 minutes into a mixture of 2.5 g iodine and 2500 g ethyl-n-butylether (bp=91.4° C.). The temperature inside the extraction vessel was maintained at 90° C. Stirring was continued for a further 30 minutes, the ether phase was separated from the catalyst complex containing promoter and distillatively separated into 2450 g ethyl-n-butylether, 360 g acetic acid/acetic anhydride/EDA-mixture and 52.5 g organic contaminants (containing 0.008 mass % Rh) which were discarded. The purified catalyst complex containing promoter was united with the AcOH/Ac$_2$O/EDA-mixture recovered from the ether phase and a further 50 g residual ethyl-n-butlyether was distilled off; 950 g purified catalyst solution containing 11.2 g Rh was then recycled into the catalyst cycle. 99.96 % rhodium was recycled. The united ether distillates were recycled into the extraction stage.

We claim:

1. A process for purifying and recovering catalyst solution contaminated during the carbonylation of at least one substance selected from the group consisting of methyl acetate and dimethylether, containing carbonyl complexes of rhodium, quaternary heterocyclic aromatic nitrogen compounds or quaternary organophosphorus compounds as organic promoters, undistillable organic contaminants as well as acetic acid, acetic anhydride and ethylidene diacetate, which comprises: subjecting the contaminated catalyst solution, in a first processing stage, to extraction with a dialkylether having from 1–4 carbon atoms and thereby freeing it from its organic contaminants, from acetic acid, acetic anhydride and ethylidene diacetate, and separating the ether phase from a precipitated promoter-containing catalyst complex; treating the ether phase, in a second processing stage, with iodine or methyl iodide, separating a further portion of precipitated promoter-containing catalyst complex and uniting it with the purified catalyst complex coming from the first processing stage; separating the ether phase into its constituents by distilling it, using recovered dialkylether again in the extraction of the first processing stage, preparing fresh catalyst solution from the recovered mixture of acetic acid, acetic anhydride and ethylidene diacetate and united purified catalyst complex, and expelling the organic contaminants retained in the residue of the ether phase distillation; and distillatively freeing the purified catalyst solution from residual dialkyl ether.

2. A process as claimed in claim 1, wherein the catalyst solution is extracted with the dialkylether and the ether phase is treated with iodine or methyl iodide at temperatures of 20°–140° C. and under pressures of 1–30 bars.

3. A process as claimed in claim 1, wherein 0.5–20 parts by weight dialkylether is used per part by weight contaminated catalyst solution.

4. Process as claimed in claim 1, wherein 0.00005–0.01 part by weight iodine or iodine methyl iodide is used per part by weight dialkylether.

5. A process as claimed in claim 1, wherein the first and second processing stages are combined by treating the contaminated catalyst solution with iodine or methyl iodide and dialkylether and the ether phase is separated from the precipitated promoter-containing catalyst complex.

6. A process as claimed in claim 5, wherein 0.0001–0.01 part by weight iodine or methyl iodide is used per part by weight contaminated catalyst solution.

* * * * *